United States Patent [19]

Kurian et al.

[11] Patent Number: 5,840,957

[45] Date of Patent: Nov. 24, 1998

[54] TRANSESTERIFICATION PROCESS USING LANTHANUM COMPOUND CATALYST

[75] Inventors: Joseph Varapadavil Kurian; Yuanfeng Liang, both of Newark, Del.

[73] Assignee: E. I. du Pont de Nemours and Company, Wilmington, Del.

[21] Appl. No.: 42,525

[22] Filed: Mar. 16, 1998

[51] Int. Cl.$^6$ .................................................. C07C 67/02
[52] U.S. Cl. ............................................................ 560/92
[58] Field of Search .................................................. 560/92

[56] References Cited

U.S. PATENT DOCUMENTS

| | | | |
|---|---|---|---|
| 2,820,023 | 1/1958 | Cavanaugh et al. | 260/75 |
| 3,489,722 | 1/1970 | Kotani et al. | 260/75 |
| 3,532,671 | 10/1970 | Carlson et al. | 260/75 |
| 3,671,379 | 6/1972 | Evans et al. | 161/173 |
| 3,847,873 | 11/1974 | Jackson et al. | 260/75 R |
| 5,208,297 | 5/1993 | Ford et al. | 525/415 |

OTHER PUBLICATIONS

CASPLUS Online Printou, 1995:836424, Abstract of Polym Sci 1995, 58(4) 771–7, 1995.

*Primary Examiner*—Samuel Barts

[57] ABSTRACT

This invention relates to an improved transesterification process for the preparation of bis(3-hydroxypropyl) terephthalate monomer from 1,3-propanediol and a dialkyl terephthalate using a lanthanum compound transesterification catalyst.

7 Claims, 5 Drawing Sheets

TRANSESTERIFICATION PROCESS USING LANTHANUM COMPOUND CATALYST

BACKGROUND OF THE INVENTION

1. Field of the Invention

This invention relates to a process for making bis(3-hydroxypropyl) terephthalate monomer from a $C_1$–$C_4$ dialkyl ester of terephthalic acid and 1,3-propanediol in the presence of a lanthanum compound transesterification catalyst.

2. Description of Related Art

Preparation of polyester resins by transesterification of a $C_1$–$C_4$ dialkyl ester of terephthalic acid and a diol, followed by polycondensation is well known in the art.

Generally, the $C_1$–$C_4$ dialkyl ester of terephthalic acid and the diol are reacted in the presence of a transesterification catalyst at elevated temperature and atmospheric pressure to form a monomer and a $C_1$–$C_4$ alkanol corresponding to the $C_1$–$C_4$ alkanol components of the dialkyl ester of terephthalic acid. The $C_1$–$C_4$ alkanol is removed as it is formed during the reaction. Oligomers having a degree of polymerization of about 4 or less can also be formed. The monomer and any oligomer can then be polymerized at higher temperatures under reduced pressure in the presence of a polycondensation catalyst to form the desired polyester resin. These reactions can be carried out in batch or continuous processes.

Transesterification catalysts known in the art include titanium, manganese and zinc compounds. For example, Evans et al, in U.S. Pat. No. 3,671,379, disclose a process for producing poly(trimethylene terephthalate) using a titanium catalyst in both the transesterification and polycondensation reactions. Cerium and lead acetylacetonate catalysts for the transesterification of dimethyl terephthalate with ethylene glycol are disclosed by Carlson et al in U.S. Pat. No. 3,532,671. Lanthanum compounds, such as lanthanum acetate, are disclosed by Cavanaugh et al in U.S. Pat. No. 2,820,023 to be effective transesterification catalysts for the preparation of bis(2-hydroxyethyl) terephthalate from dimethyl terephthalate (DMT) and ethylene glycol.

New process improvements which increase transesterification rates resulting in increased throughput and reduced cost of production of bis(3-hydroxypropyl) terephthalate monomer are of significant interest to the chemical industry.

SUMMARY OF THE INVENTION

The present invention is directed to such a new improved process for making bis(3-hydroxypropyl) terephthalate monomer, comprising contacting a $C_1$–$C_4$ dialkyl ester of terephthalic acid with 1,3-propanediol in the presence of a lanthanum compound transesterification catalyst selected from the group consisting of a lanthanum beta-diketonate, a lanthanum beta-ketoester, a lanthanum beta-diester and mixtures thereof at a temperature from about 155° C. to about 245° C. with a mole ratio of the 1,3-propanediol to the dialkyl ester of about 1.1:1 to about 2.2:1.

BRIEF DESCRIPTION OF THE DRAWINGS

The invention can be more fully understood from the following detailed description thereof in connection with accompanying drawings described as follows.

DESCRIPTION OF THE PREFERRED EMBODIMENT(S)

The invention is a transesterification process for making bis(3-hydroxypropyl) terephthalate monomer. A $C_1$–$C_4$ dialkyl ester of terephthalic acid is contacted or combined with 1,3-propanediol in the presence of a lanthanum compound transesterification catalyst selected from the group consisting of a lanthanum beta-diketonate, a lanthanum beta-ketoester, a lanthanum beta-diester, and mixtures thereof. The process is conducted at a temperature from about 155° C. to about 245° C. with a mole ratio of the 1,3-propanediol to the dialkyl ester of about 1.1:1 to about 2.2:1.

The $C_1$–$C_4$ dialkyl esters of terephthalic acid which are suitable as reactants in the process of the current invention include dimethyl terephthalate, diethyl terephthalate, di-n-propyl terephthalate, di-isopropyl terephthalate, di-n-butyl terephthalate, di-isobutyl terephthalate, and di-t-butyl terephthalate. These $C_1$–$C_4$ dialkyl esters of terephthalic acid are diesters that are the reaction product of terephthalic acid and an alkanol containing 1–4 carbons. Preferably, the dialkyl ester is dimethyl terephthalate (DMT).

One or more other diol (other than 1,3-propanediol) in an amount less than about 10 mole percent based on the total diol (including the 1,3-propanediol and the other diol), and/or one or more other $C_1$–$C_4$ dialkyl ester of a dicarboxylic acid (other than terephthalic acid) in an amount less than about 10 mole percent based on the total $C_1$–$C_4$ dialkyl ester of dicarboxylic acid (including the $C_1$–$C_4$ dialkyl ester of terephthalic acid and the other $C_1$–$C_4$ dialkyl ester of a dicarboxylic acid), can be added before or during the transesterification reaction, followed by a polycondensation reaction to form copolymers. For instance, the diol (other than 1,3-propanediol) can be ethylene glycol, 1,4-butanediol, or mixtures thereof. The dicarboxylic acid or diacid (other than terephthalic acid) can be isophthalic acid, 2,6-naphthalene dicarboxylic acid, adipic acid, or mixtures thereof.

The lanthanum (La) compounds useful as transesterification catalysts in the present invention include lanthanum beta-diketonate compounds, lanthanum beta-ketoester compounds, lanthanum beta-diester compounds, and mixtures thereof. The lanthanum beta-diketonate compounds useful as transesterification catalysts in the process of the current invention include lanthanum tris(acetylacetonate) (also known as La(acac)$_3$) and lanthanum tris(2,2,6,6,-tetramethyl-3,5-heptanedionate) (also known as lanthanum t-butylacetylacetonate or La(t-Bu-acac)$_3$). Other lanthanum beta-diketonate compounds useful as the catalyst in the current invention include those mentioned by Ford et al in U.S. Pat. No. 5,208,297, such as, tris(t-butylhydroxymethylene-d,l-camphorato) lanthanum, lanthanum tris(2,2,6-trimethyloctan-3,5-dionate), lanthanum tris (hexafluoroacetylacetonate), and lanthanum tris (trifluoroacetylacetonate). The preferred lanthanum beta-diketonate compounds are lanthanum tris(acetylacetonate)

and lanthanum tris(2,2,6,6,-tetramethyl-3,5-heptanedionate), and the most preferred is lanthanum tris (acetylacetonate). U.S. Pat. No. 5,208,297 discloses how to make both of these preferred lanthanum beta-diketonate compounds. U.S. Pat. No. 5,208,297 also discloses lanthanum beta-ketoester compounds, such as lanthanum tris (methylacetoacetate), and lanthanum beta-diester compounds, such as lanthanum tris(dialkylmalonate), which are useful as transesterification catalysts in the process of the current invention. The lanthanum compound transesterification catalyst can be used whether it is in anhydrous or hydrate form.

The lanthanum compound catalysts are added to the transesterification reaction in concentrations corresponding to about 10 ppm to about 530 ppm, preferably to about 35 ppm to about 320 ppm of elemental lanthanum based on $C_1$–$C_4$ dialkyl ester added to the reaction. When dimethyl terephthalate is the dialkyl ester used in the reaction, the lanthanum compound catalysts are preferably added in concentrations corresponding to about 50 ppm to about 300 ppm of lanthanum based on dimethyl terephthalate. The catalyst can be added directly to the contacted or combined reactants, or added as a solution in 1,3-propanediol.

The transesterification process of the current invention can be conducted by reacting the $C_1$–$C_4$ dialkyl ester of terephthalic acid with the 1,3-propanediol in the presence of the lanthanum compound catalyst at about atmospheric pressure and at a temperature from about 155 degrees Centigrade (°C.) to about 245° C., preferably about 180° C. to about 240° C. with a mole ratio of 1,3-propanediol to $C_1$–$C_4$ dialkyl ester of terephthalic acid of about 1.1:1 to about 2.2:1, preferably about 1.4:1 to about 2.0:1. Residence times of reactants and resulting product in a reaction vessel in which the transesterification reaction occurs are generally from about 0.5 hours to about 4 hours.

Preferably, the reaction vessel is purged with an inert gas, such as nitrogen, before heating. Further, the liquid mixture in the reaction vessel can be stirred. The process can be performed in batch or continuous processes.

In the transesterification process, the $C_1$–$C_4$ dialkyl ester of terephthalic acid reacts with the 1,3-propanediol to form bis(3-hydroxypropyl) terephthalate monomer. Depending on the relative concentration of reactants and process conditions, the reaction can also produce oligomers of the monomer having a degree of polymerization of about 4 or less.

The $C_1$–$C_4$ dialkyl esters of terephthalic acid suitable for use in this invention react with 1,3-propanediol to form bis(3-hydroxypropyl) terephthalate and a monohydric alcohol. The monohydric alcohol is a $C_1$–$C_4$ alkanol corresponding to the $C_1$–$C_4$ alkanol components of the dialkyl ester of terephthalic acid. Thus, the monohydric alcohol, or the $C_1$–$C_4$ alkanol, is methanol, ethanol, propanol, or butanol. For example, 1,3-propanediol is reacted with dimethyl terephthalate in the presence of a lanthanum compound transesterification catalyst to form bis(3-hydroxypropyl) terephthalate and methanol.

Other typically undesired byproducts can be formed including allyl alcohol, acrolein and acrylic acid which can be minimized or eliminated by a proper selection of the relative concentration of reactants and process conditions.

The $C_1$–$C_4$ alkanol can be removed by distillation as it is formed during the reaction. This separates bis(3-hydroxypropyl) terephthalate monomer and any oligomers thereof from a product of the reaction. The bis(3-hydroxypropyl) terephthalate monomer can be polymerized to form poly(trimethylene terephthalate) which has a number of end uses including but not limited to carpeting, hosiery, fishing line, films, and papermaking press fabrics.

High quality poly(trimethylene terephthalate) can be made from bis(3-hydroxypropyl) terephthalate monomer and oligomers thereof using polycondensation methods known in the art. For example, after transesterification, the temperature can be raised to be in the range of about 240° C. to about 290° C. and the pressure can be reduced to below about 1 mm of mercury absolute pressure in the presence of a suitable catalyst, such as titanium or antimony compounds, to polymerize the monomer and oligomers thereof with removal of excess 1,3-propanediol.

As illustrated in Examples 1–3 versus Comparative Examples A–C, lanthanum beta-diketonate compounds such as lanthanum tris(acetylacetonate) have been found to provide significantly faster transesterification rates than lanthanum acetate for the reaction of 1,3-propanediol with dimethyl terephthalate. Improved rates increase throughput and reduce the cost of production of poly(trimethylene terephthalate) monomer. Alternatively, less catalyst can be used compared to lanthanum acetate. Surprisingly, as illustrated in Comparative Examples D–G, lanthanum beta-diketonate catalysts do not result in a similar improvement in rate over lanthanum acetate catalyst for the reaction of ethylene glycol or 1,4-butanediol with dimethyl terephthalate.

TEST METHODS

Hunter color lab measurements were measured according to ASTM D2244.

Intrinsic viscosity having units of deciliter/gram or dl/g was determined by measuring the flow times of a polymer solution after successive dilutions with fresh solvent, calculating the reduced viscosities, and extrapolating a plot of the reduced viscosities against concentration to zero concentration. The reduced viscosity is calculated as:

$$\left[ \frac{\text{Flow time of polymer solution}}{\text{Flow time of solvent}} - 1 \right] \times \frac{1}{c}$$

where c is the concentration expressed as grams (g) of polymer per 100 milliliters (ml) of solvent. The intrinsic viscosity was measured at 25° C. in a modified Ostwald viscometer using trifluoroacetic acid/dichloromethane (50/50, w/w) as the solvent.

EXAMPLE 1

This example demonstrates the transesterification reaction of dimethyl terephthalate with 1,3-propanediol using lanthanum tris(acetylacetonate) hydrate as the transesterification catalyst (150 ppm La based on the theoretical weight of the final polymer) to form bis(3-hydroxypropyl) terephthalate.

A 250 ml flask equipped with a stirrer and distillation column was charged with 58.5 g of dimethyl terephthalate (DMT) and 41 g of 1,3-propanediol (purchased from Degussa AG, with offices in Wolfgang, Germany) for a mole ratio of 1,3-propanediol:DMT of 1.8:1. The flask was then purged with nitrogen and the contents of the flask were heated. When the temperature inside the flask reached about 150° C. and all of the DMT had melted, the stirrer was started. When the temperature reached 210° C., 30 mg of lanthanum tris(acetylacetonate) hydrate (purchased from Strem Chemicals, of Newburyport, Mass.) (150 ppm of lanthanum based on final polymer, 160 ppm based on DMT) was added.

The concentration of lanthanum was calculated based on the weight of hydrate added, using the molecular weight for anhydrous lanthanum tris(acetylacetonate). Upon addition of the lanthanum tris(acetylacetonate) hydrate, methanol was evolved. The methanol was removed as a liquid condensate by distillation. The total liquid condensate was assumed to be methanol for purposes of this Example because the amount of methanol is more than 99% of the condensate in such a procedure. The temperature was held at 210° C. and the amount of liquid methanol collected was measured every ten minutes until no more methanol was evolved. The cumulative amount of methanol collected vs. time is shown in Table 1 and FIG. 1. A total of 21.5 ml of methanol was collected in 40 minutes. The theoretical amount of methanol for complete transesterification is 24.4 ml. Some methanol may have been flushed away with the nitrogen purge and small amounts may have remained in the reaction mixture and been removed upon application of vacuum during polycondensation.

After evolution of methanol, the resulting monomer, bis(3-hydroxypropyl) terephthalate, was polymerized in the same reaction vessel at a temperature of 250° C. and a pressure of 0.4 mm Hg, using a titanate compound as the polycondensation catalyst (commercially available from E. I. du Pont de Nemours and Company, of Wilmington, Del.). The poly(trimethylene terephthalate) resin obtained had an intrinsic viscosity of 0.859 dl/g and melting point of 230° C. (measured as the peak on the differential scanning calorimeter (dsc) endotherm). The polymer had a L=77.2 and b=1.96 (in Hunter Lab color measurement units).

Results for Examples 1–3 and Comparative Examples A–C are discussed after Table 2.

EXAMPLE 2

This example demonstrates the transesterification reaction of dimethyl terephthalate with 1,3-propanediol using lanthanum tris(acetylacetonate) hydrate as the transesterification catalyst (100 ppm La based on final polymer) to form bis(3-hydroxypropyl) terephthalate.

The procedure of Example 1 was followed except that 20 mg of lanthanum tris(acetylacetonate) hydrate (100 ppm of lanthanum based on final polymer, 110 ppm based on DMT) was used as the transesterification catalyst. The amount of methanol collected vs. time is shown in Table 1 and FIG. 1. A total of 21 ml of methanol was collected in 40 minutes.

EXAMPLE 3

This example demonstrates the transesterification reaction of dimethyl terephthalate with 1,3-propanediol using lanthanum tris(acetylacetonate) hydrate as the transesterification catalyst (50 ppm La based on final polymer) to form bis(3-hydroxypropyl) terephthalate.

The procedure of Example 1 was followed except that 10 mg of lanthanum tris(acetylacetonate) hydrate (50 ppm of lanthanum based on final polymer, 55 ppm based on DMT) was used as the transesterification catalyst. The amount of methanol collected vs. time is shown in Table 1 and FIG. 1. A total of 20.5 ml of methanol was collected in 60 minutes.

TABLE 1

| | Methanol Evolution vs. Time using La(acac)$_3$ Hydrate | | |
| --- | --- | --- | --- |
| Time (min.) | Example 1 150 ppm La MeOH (ml) | Example 2 100 ppm La MeOH (ml) | Example 3 50 ppm La MeOH (ml) |
| 0 | 0 | 0 | 0 |
| 10 | 18.5 | 15.5 | 9 |
| 20 | 21 | 20 | 14.5 |
| 30 | 21 | 20.5 | 18 |
| 40 | 21.5 | 21 | 19 |
| 50 | | | 20 |
| 60 | | | 20.5 |

COMPARATIVE EXAMPLE A

This example demonstrates the transesterification reaction of dimethyl terephthalate with 1,3-propanediol using lanthanum acetate monohydrate as the transesterification catalyst (150 ppm La based on final polymer) to form bis(3-hydroxypropyl) terephthalate.

The procedure of Example 1 was followed except 22 mg of lanthanum acetate monohydrate (99.9%, purchased from Aldrich Chemical Co., of Milwaukee, Wis.) (150 ppm of lanthanum based on final polymer, 155 ppm based on DMT) was added as the transesterification catalyst. The amount of methanol collected vs. time is shown in the Table 2 and FIG. 1. A total of 22 ml of methanol was collected in 50 minutes. The theoretical amount of methanol for complete transesterification is 24.4 ml.

COMPARATIVE EXAMPLE B

This example demonstrates the transesterification reaction of dimethyl terephthalate with 1,3-propanediol using lanthanum acetate monohydrate as the transesterification catalyst (100 ppm La based on final polymer) to form bis(3-hydroxypropyl) terephthalate.

The procedure of Example 1 was followed except that 15 mg of lanthanum acetate monohydrate (100 ppm of lanthanum based on final polymer, 110 ppm based on DMT) was used as the transesterification catalyst. The amount of methanol collected vs. time is shown in Table 2 and FIG. 1. A total of 21 ml of methanol was collected in 80 minutes.

COMPARATIVE EXAMPLE C

This example demonstrates the transesterification reaction of dimethyl terephthalate with 1,3-propanediol using lanthanum acetate monohydrate as the transesterification catalyst (50 ppm La based on final polymer) to form bis(3-hydroxypropyl) terephthalate.

The procedure of Example 1 was followed except that 7 mg of lanthanum acetate monohydrate (50 ppm of lanthanum based on final polymer, 50 ppm based on DMT) was used as the transesterification catalyst. The amount of methanol collected vs. time is shown in Table 2 and FIG. 1. A total of 13.5 ml of methanol was collected in 90 minutes, after which the measurements were stopped, although methanol continued to be evolved at a slow rate.

TABLE 2

Methanol Evolution vs. Time using La(Ac)₃ Hydrate

| Time (min) | Example A 150 ppm La MeOH (ml) | Example B 100 ppm La MeOH (ml) | Example C 50 ppm La MeOH (ml) |
|---|---|---|---|
| 0 | 0 | 0 | 0 |
| 10 | 12.5 | 6 | 4 |
| 20 | 20 | 10.5 | 6 |
| 30 | 21.5 | 13.5 | 8 |
| 40 | 22 | 16.5 | 9.5 |
| 50 | 22 | 18.5 | 10.5 |
| 60 |  | 19.5 | 11 |
| 70 |  | 20.5 | 12 |
| 80 |  | 21 | 12.5 |
| 90 |  |  | 13.5 |

Figure 1:
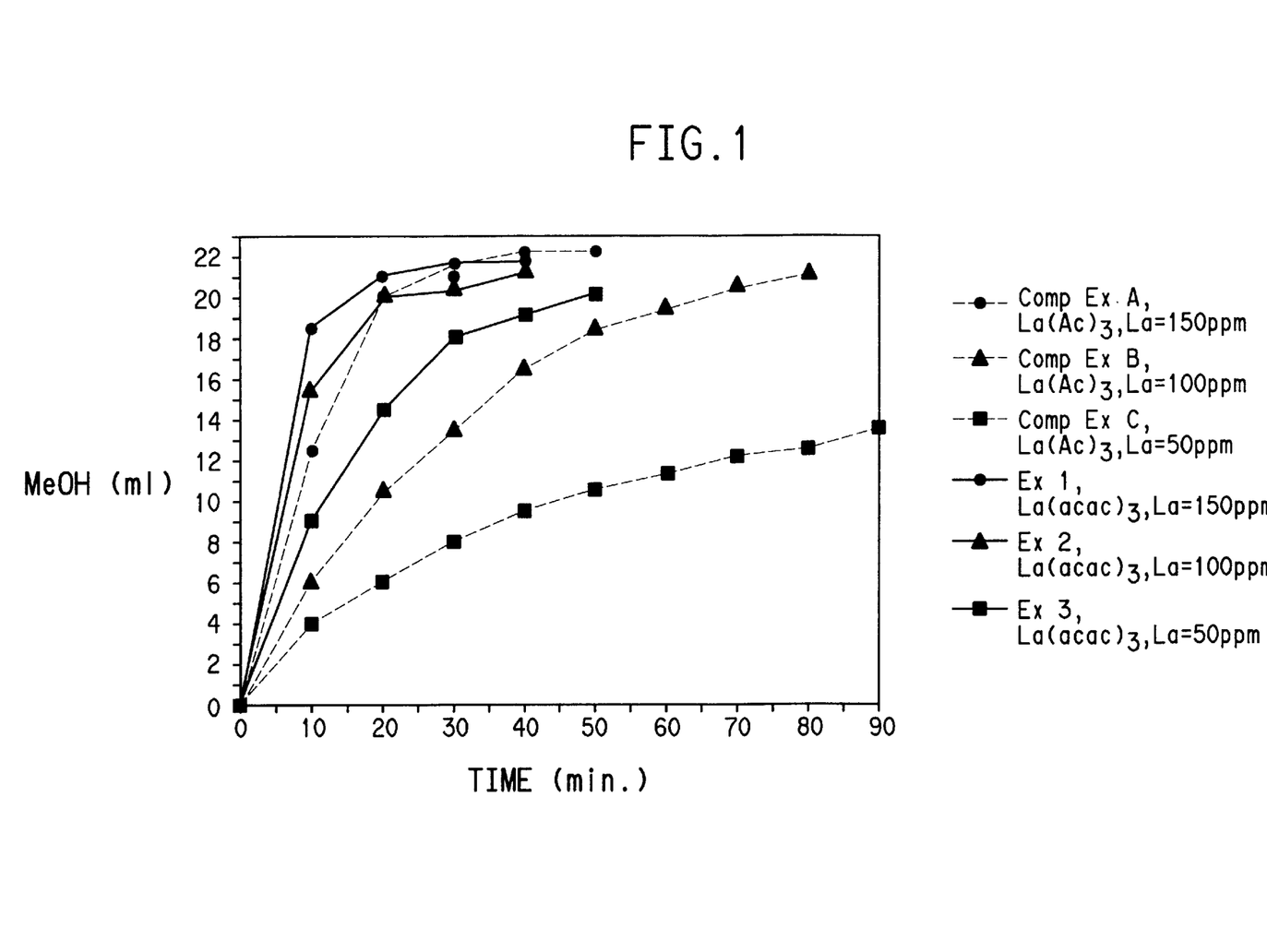
FIG. 1 is a plot depicting the amount of methanol collected versus time for Examples 1–3 illustrating the invention and Comparative Examples A–C.

FIG. 1 demonstrates that at 50 and 100 ppm La based on polymer, the rate of transesterification is significantly higher when lanthanum tris(acetylacetonate) hydrate (Examples 3 and 2) is used as the catalyst versus lanthanum acetate monohydrate (Comparative Examples C and B). At 150 ppm lanthanum (Example 1), the initial rate is higher using lanthanum tris(acetylacetonate) hydrate catalyst; however, the corresponding concentration of lanthanum acetate monohydrate curve (Comparative Example A) intersects the lanthanum tris(acetylacetonate) hydrate curve (Example 1) at approximately 25 minutes reaction time. The higher initial rate using lanthanum tris(acetylacetonate) hydrate catalyst will provide higher throughput in a continuous polymerization process where resident times are typically shorter than in batch processes.

EXAMPLE 4

This example demonstrates the transesterification reaction of dimethyl terephthalate with 1,3-propanediol using anhydrous lanthanum tris(acetylacetonate) as the transesterification catalyst (100 ppm La based on final polymer) to form bis(3-hydroxypropyl) terephthalate.

Figure 2:
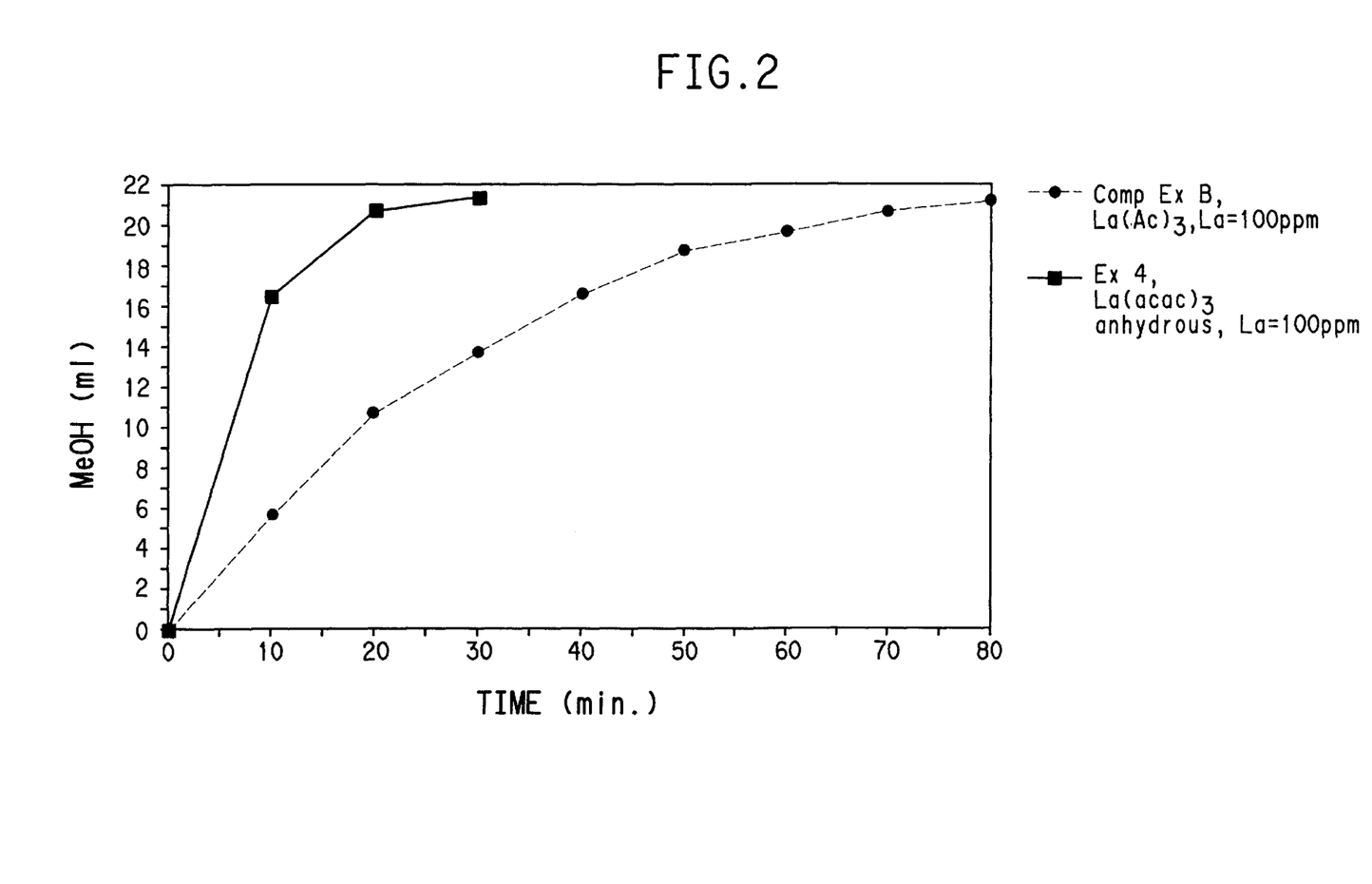
FIG. 2 is a plot depicting the amount of methanol collected versus time for Examples 2 and 4 illustrating the invention and Comparative Example B.

The procedure of Example 1 was followed except that 19 mg of anhydrous lanthanum tris(acetylacetonate) (purchased from Strem Chemicals, of Newburyport, Mass.) (100 ppm of lanthanum based on final polymer, 105 ppm based on DMT) was used as the transesterification catalyst. The amount of methanol collected vs. time is shown in Table 3 and FIG. 2. A total of 21 ml of methanol was collected in 30 minutes. The theoretical amount of methanol for complete transesterification is 24.4 ml. The rate of transesterification using anhydrous lanthanum tris(acetylacetonate) is also significantly higher than the transesterification rate using lanthanum acetate monohydrate in Comparative Example B, in which only 13.5 ml of methanol were collected in 30 minutes.

TABLE 3

Methanol Evolution vs. Time using 100 ppm La Catalyst

| Time (min) | Example B La(ac)3 MeOH (ml) | Example 4 La(acac)3 anhydrous MeOH (ml) |
|---|---|---|
| 0 | 0 | 0 |
| 10 | 6 | 16.5 |
| 20 | 10.5 | 20.5 |
| 30 | 13.5 | 21 |
| 40 | 16.5 |  |
| 50 | 18.5 |  |
| 60 | 19.5 |  |
| 70 | 20.5 |  |
| 80 | 21 |  |

EXAMPLE 5

This example demonstrates the transesterification reaction of dimethyl terephthalate with 1,3-propanediol using lanthanum t-butylacetylacetonate (otherwise known as tris(2, 2,6,6-tetramethyl-3,5-heptanedionato)lanthanum or La(t-Bu-acac)₃) as the transesterification catalyst (100 ppm La based on final polymer) to form bis(3-hydroxypropyl) terephthalate.

Figure 3:
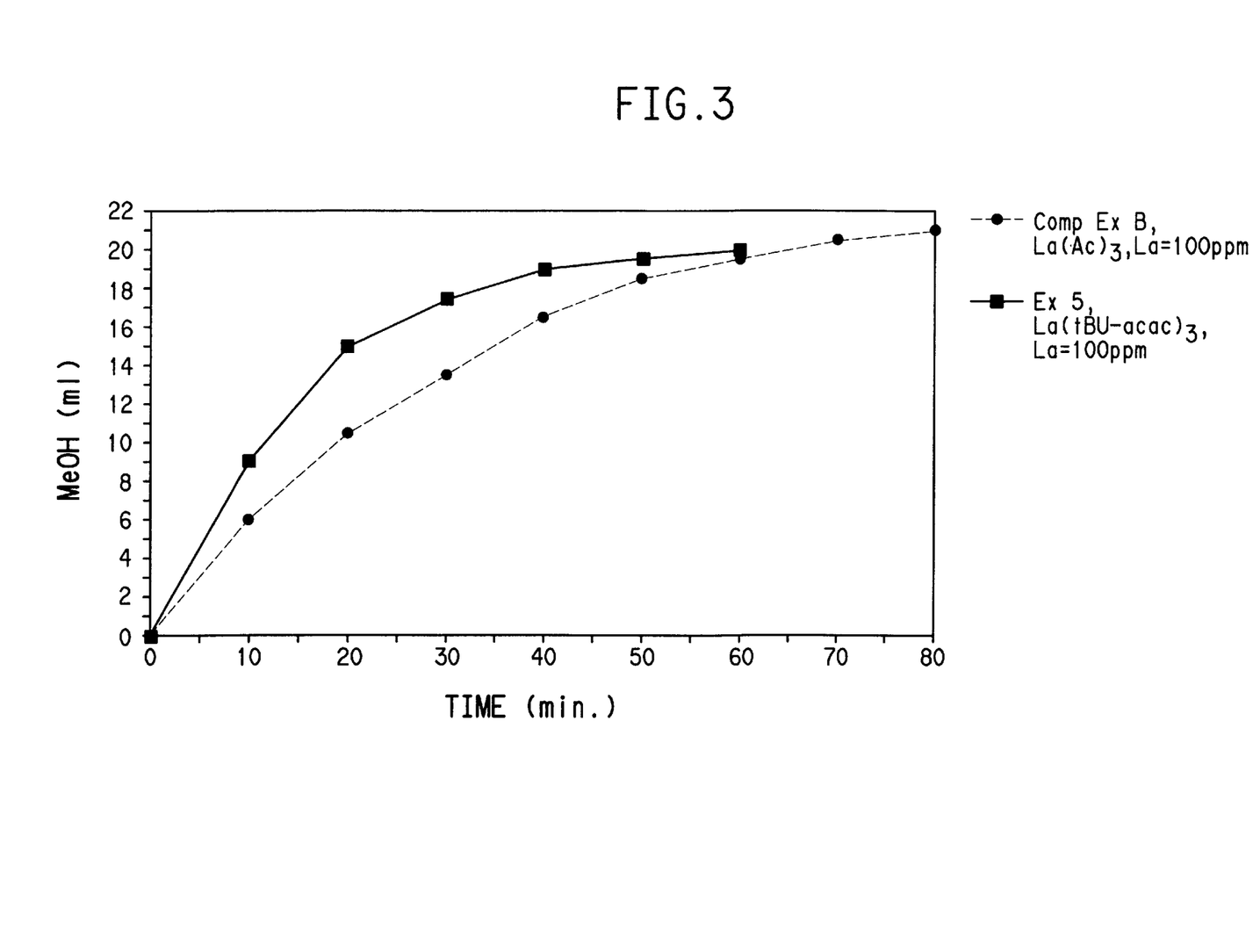
FIG. 3 is a plot depicting the amount of methanol collected versus time for Example 5 illustrating the invention and Comparative Example B.

The process of Example 1 was followed except that 31 mg of lanthanum t-butylacetylacetonate (Aldrich Chemical Co., Milwaukee, Wis.) (100 ppm of lanthanum based on final polymer, 110 ppm based on DMT) was used as the transesterification catalyst. The amount of methanol collected vs. time is shown in Table 4 and FIG. 3. A total of 20 ml of methanol was collected in 60 minutes. The theoretical amount of methanol for complete transesterification is 24.4 ml. As illustrated in FIG. 3, the initial rate of transesterification is greater for the lanthanum t-butylacetylacetonate catalyst in this Example 5 than for the lanthanum acetate monohydrate catalyst used in Comparative Example B.

TABLE 4

Methanol Evolution vs. Time using 100 ppm La Catalyst

| La(Ac)₃ Time (min) | Example B La(t-Bu-acac)₃ La = 100 ppm MeOH (ml) | Example 5 La = 100 ppm MeOH (ml) |
|---|---|---|
| 0 | 0 | 0 |
| 10 | 6 | 9 |
| 20 | 10.5 | 15 |
| 30 | 13.5 | 17.5 |
| 40 | 16.5 | 19 |
| 50 | 18.5 | 19.5 |
| 60 | 19.5 | 20 |
| 70 | 20.5 |  |
| 80 | 21 |  |

COMPARATIVE EXAMPLE D

This example demonstrates the transesterification reaction of dimethyl terephthalate with ethylene glycol using lanthanum acetate monohydrate as the transesterification catalyst (100 ppm La based on final polymer) to form bis(2-hydroxyethyl) terephthalate.

Figure 4:
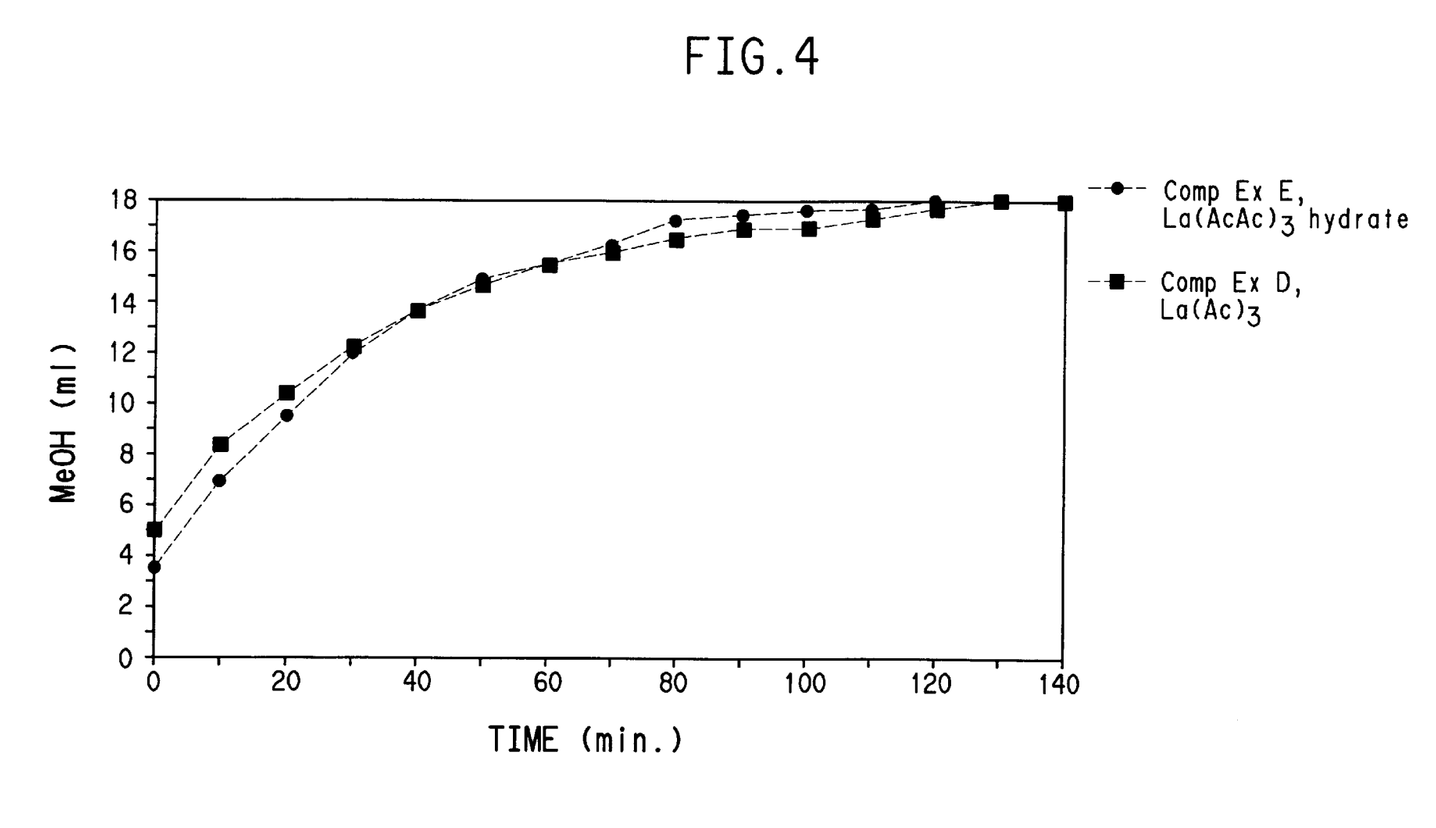
FIG. 4 is a plot depicting the amount of methanol collected versus time for Comparative Examples D and E.

A 250 ml flask equipped with a distillation column and stirrer was charged with 58.5 g of dimethyl terephthalate (DMT) and 34 g of ethylene glycol for a mole ratio of ethylene glycol to DMT of 1.8:1. The flask was then purged with nitrogen and the contents of the flask were heated. When the temperature inside the flask reached about 150° C. and all of the DMT had melted, the stirrer was started. When the temperature reached 200° C., 14 mg of lanthanum acetate monohydrate (100 ppm of lanthanum on final polymer, 100 ppm based on DMT) was added. Upon addition of the lanthanum acetate monohydrate, methanol was evolved. The methanol was recovered as a liquid by distillation. The temperature was held at 200° C. and the amount of methanol collected was measured every ten minutes until no more methanol was evolved. The amount of methanol collected vs. time are shown in Table 5 and FIG. 4. A total of 18 ml of methanol was collected in 140 minutes. The theoretical amount of methanol for complete transesterification is 24.4 ml. The results of this Comparative Example D are discussed in Comparative Example E.

COMPARATIVE EXAMPLE E

This example demonstrates the transesterification reaction of dimethyl terephthalate with ethylene glycol using lanthanum tris(acetylacetonate) hydrate as the transesterification catalyst (100 ppm La based on final polymer) to form bis(2-hydroxyethyl) terephthalate.

The procedure of Comparative Example D was followed except that 19 mg of lanthanum tris(acetylacetonate) hydrate (100 ppm of lanthanum based on final polymer, 105 ppm based on DMT) was added. The amount of methanol collected vs. time is shown in Table 5 and FIG. 4. A total of 17.8 ml of methanol was collected in 130 minutes.

The results of Examples D and E demonstrate that the rate of transesterification using lanthanum tris(acetylacetonate) hydrate catalyst is similar to that for lanthanum acetate monohydrate catalyst for the reaction of DMT with ethylene glycol.

Surprisingly, as demonstrated in Example 2 and Comparative Example B, the rate of reaction of DMT with 1,3-propanediol in the process of the current invention using lanthanum tris(acetylacetonate) hydrate catalyst at 100 ppm La is significantly faster than the rate using lanthanum acetate monohydrate catalyst.

TABLE 5

Methanol Evolution for Transesterification of Ethylene Glycol and DMT using 100 ppm La Based on Final Polymer

| Time (min) | Example D La(Ac)3 MeOH (ml) | Example E La(acac)3 hydrate MeOH (ml) |
|---|---|---|
| 0 | 4.8 | 3.5 |
| 10 | 8.5 | 7 |
| 20 | 10.5 | 9.5 |
| 30 | 12.2 | 12 |
| 40 | 13.5 | 13.5 |
| 50 | 14.5 | 14.8 |
| 60 | 15.5 | 15.5 |
| 70 | 16 | 16.2 |
| 80 | 16.5 | 17 |
| 90 | 16.8 | 17.2 |
| 100 | 17 | 17.5 |
| 110 | 17.2 | 17.5 |
| 120 | 17.5 | 17.8 |
| 130 | 17.8 | 17.8 |
| 140 | 18 | |

COMPARATIVE EXAMPLE F

This example demonstrates the transesterification reaction of dimethyl terephthalate with 1,4-butanediol using lanthanum acetate monohydrate as the transesterification catalyst (150 ppm La based on final polymer) to form bis(4-hydroxybutyl) terephthalate.

Figure 5:
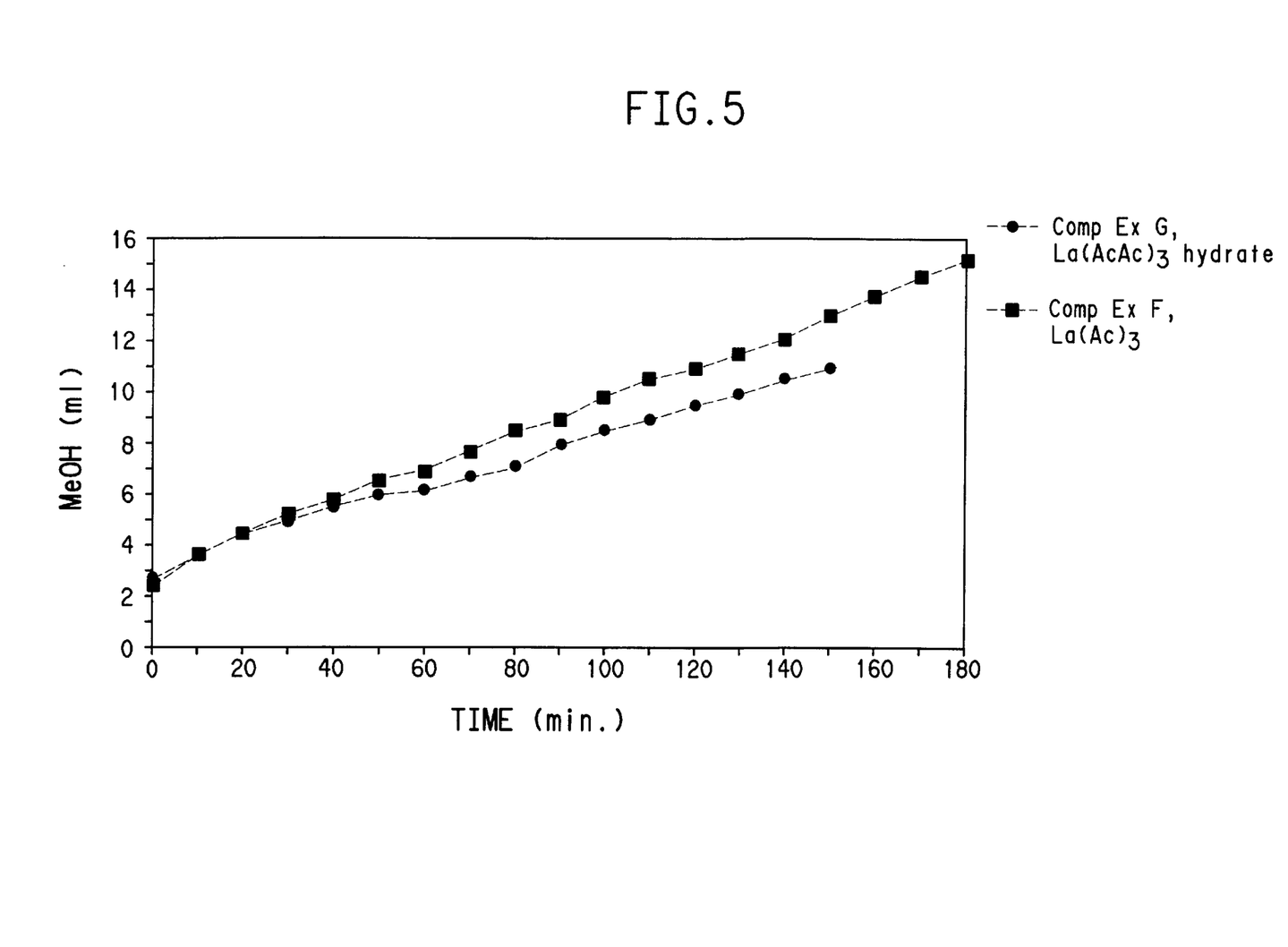
FIG. 5 is a plot depicting the amount of methanol collected versus time for Comparative Examples F and G.

A 250 ml flask equipped with a stirrer and distillation column was charged with 58.5 g of dimethyl terephthalate (DMT) and 49 g of 1,4-butanediol for a mole ratio of 1,4-butanediol:DMT of 1.8:1. The flask was then purged with nitrogen and the contents of the flask were heated. When the temperature inside the flask had reached about 150° C. and all of the DMT had melted, the stirrer was started. When the temperature had reached 210° C., 24 mg of lanthanum acetate monohydrate (150 ppm of lanthanum on final polymer, 170 ppm based on DMT) was added. Upon addition of the lanthanum acetate, methanol was evolved. The methanol was recovered as a liquid by distillation. The temperature was kept at 210° C. and the amount of methanol collected was measured every ten minutes until no more methanol was evolved. The amount of methanol collected vs. time is shown in Table 6 and FIG. 5. A total of 15.2 ml of methanol was collected in 180 minutes. The theoretical amount of methanol for complete transesterification is 24.4 ml. The results are discussed in Comparative Example G.

COMPARATIVE EXAMPLE G

This example demonstrates the transesterification reaction of dimethyl terephthalate with 1,4-butanediol using lanthanum tris(acetylacetonate) hydrate as the transesterification catalyst (150 ppm La based on final polymer) to form bis(4-hydroxybutyl) terephthalate.

The procedure of Comparative Example F was followed except that 31 mg of lanthanum tris(acetylacetonate) hydrate (150 ppm based on final polymer, 168 ppm based on DMT) was used as the transesterification catalyst. The amounts of methanol collected vs. time are shown in Table 6 and FIG. 5. A total of 11 ml of methanol was collected in 150 minutes.

The results of Comparative Examples F and G demonstrate that the rate of transesterification using La(Ac)$_3$ catalyst is somewhat greater than that for La(acac)$_3$ catalyst for the reaction of DMT with 1,4-butanediol. Surprisingly, as demonstrated in Example 1 and Comparative Example A, the initial rate of reaction of DMT with 1,3-propanediol using 150 ppm La is higher using the La(acac)$_3$ catalyst than for the La(Ac)$_3$ catalyst. In addition, the rate of the transesterification of DMT with 1,3-propanediol using lanthanum tris(acetylacetonate) hydrate catalyst is significantly higher than the rate of reaction of DMT and 1,4-butanediol using the same catalyst. In the lanthanum tris(acetylacetonate) hydrate catalyzed reaction of DMT with 1,3-propanediol (Example 1), 21.5 ml of methanol were collected in 40 minutes. For comparison purposes, 5.5 ml of methanol were collected in 40 minutes in Comparative Example G for the reaction of DMT with 1,4-butanediol using the same catalyst.

TABLE 6

Methanol Evolution for Transesterification of 1,4-Butanetiol and DMT using 150 ppm La Based on Final Polymer

| Time (min) | Example F La(Ac)3 MeOH (ml) | Example G La(acac)3 MeOH (ml) |
|---|---|---|
| 0 | 2.5 | 2.8 |
| 10 | 3.8 | 3.8 |
| 20 | 4.5 | 4.5 |
| 30 | 5.2 | 5 |
| 40 | 5.8 | 5.5 |
| 50 | 6.5 | 6 |
| 60 | 7 | 6.2 |
| 70 | 7.8 | 6.8 |
| 80 | 8.5 | 7.2 |

TABLE 6-continued

Methanol Evolution for Transesterification of 1,4-Butanetiol and DMT using 150 ppm La Based on Final Polymer

| Time (min) | Example F La(Ac)3 MeOH (ml) | Example G La(acac)3 MeOH (ml) |
|---|---|---|
| 90 | 9 | 8 |
| 100 | 9.8 | 8.5 |
| 110 | 10.5 | 9 |
| 120 | 11 | 9.5 |
| 130 | 11.5 | 10 |
| 140 | 12.2 | 10.5 |
| 150 | 13 | 11 |
| 160 | 13.8 | |
| 170 | 14.5 | |
| 180 | 15.2 | |

What is claimed is:

1. A process for making bis(3-hydroxypropyl) terephthalate monomer, comprising the step of:

contacting a $C_1$–$C_4$ dialkyl ester of terephthalic acid with 1,3-propanediol in the presence of a lanthanum compound transesterification catalyst selected from the group consisting of a lanthanum beta-diketonate, a lanthanum beta-ketoester, a lanthanum beta-diester, and mixtures thereof at a temperature from about 155° C. to about 245° C. with a mole ratio of the 1,3-propanediol to the dialkyl ester of about 1.1:1 to about 2.2:1.

2. The process of claim 1, wherein the catalyst is present in a concentration of about 35 to about 300 ppm of lanthanum based on the $C_1$–$C_4$ dialkyl ester.

3. The process of claim 1, further comprising the step of:

separating bis(3-hydroxypropyl) terephthalate monomer and any oligomers thereof from a product of the contacting step.

4. The process of claim 1, wherein the lanthanum compound transesterification catalyst is selected from the group consisting of lanthanum tris(acetylacetonate), lanthanum tris(2,2,6,6,-tetramethyl-3,5-heptanedionate), tris(t-butylhydroxymethylene-d,l-camphorato) lanthanum, lanthanum tris(2,2,6-trimethyloctan-3,5-dionate), lanthanum tris(hexafluoroacetylacetonate), lanthanum tris(trifluoroacetylacetonate), lanthanum tris(methylacetoacetate), and lanthanum tris(dialkylmalonate).

5. The process of claim 1, wherein the lanthanum compound transesterification catalyst is a hydrate.

6. The process of claim 1, wherein the lanthanum compound transesterification catalyst is anhydrous.

7. The process of claim 1, further comprising:

adding one or more other diol (other than 1,3-propanediol) in an amount less than about 10 mole percent based on the total diol and/or one or more other $C_1$–$C_4$ dialkyl ester of a dicarboxylic acid (other than terephthalic acid) in an amount less than about 10 mole percent based on the total $C_1$–$C_4$ dialkyl ester of dicarboxylic acid.

* * * * *